(12) United States Patent
Chae et al.

(10) Patent No.: US 7,393,983 B2
(45) Date of Patent: Jul. 1, 2008

(54) METHOD AND APPARATUS FOR SEPARATING AROMATIC DIALDEHYDE

(75) Inventors: Jong-Hyun Chae, Daejeon (KR); Won-Ho Lee, Daejeon (KR); Dong-Il Lee, Dongducheon (KR); Hyun-Kyung Yoon, Seoul (KR)

(73) Assignee: LG Chem, Ltd., Seoul (KR)

( * ) Notice: Subject to any disclaimer, the term of this patent is extended or adjusted under 35 U.S.C. 154(b) by 64 days.

(21) Appl. No.: 11/430,201

(22) Filed: May 9, 2006

(65) Prior Publication Data

US 2006/0276678 A1 Dec. 7, 2006

(30) Foreign Application Priority Data

May 10, 2005 (KR) .................... 10-2005-0038799

(51) Int. Cl.
*C07C 45/27* (2006.01)
*C07C 45/90* (2006.01)
(52) U.S. Cl. .................................................. 568/438
(58) Field of Classification Search ................. 568/438
See application file for complete search history.

(56) References Cited

U.S. PATENT DOCUMENTS

| 2,888,488 A | 5/1959 | Nace |
| 3,845,137 A | 10/1974 | Magder |
| 3,946,067 A | 3/1976 | Kwiatek et al. |
| 4,017,547 A | 4/1977 | Simmons et al. |
| 4,465,865 A | 8/1984 | Englander et al. |
| 6,458,737 B1 | 10/2002 | Kishimoto et al. |

*Primary Examiner*—Sikarl A Witherspoon
(74) *Attorney, Agent, or Firm*—McKenna Long & Aldridge LLP

(57) ABSTRACT

The present invention relates to a method and an apparatus for continuously separating aromatic dialdehyde from a reaction mixture obtained by gas-phase oxidation of dimethylbenzene. The method for continuously separating aromatic dialdehyde includes the steps of congealing aromatic dialdehyde by cooling the gas-phase reaction mixture including the aromatic dialdehyde, which is obtained by gas-phase oxidation of dimethylbenzene, to 5-70° C. and separating the congealed aromatic dialdehyde from the remaining reaction mixture. Using the method and apparatus in accordance with the present invention, aromatic dialdehyde can be effectively and selectively separated from a reaction mixture obtained by gas-phase oxidation of dimethylbenzene in high yield.

7 Claims, 2 Drawing Sheets

METHOD AND APPARATUS FOR SEPARATING AROMATIC DIALDEHYDE

CROSS REFERENCES TO RELATED APPLICATION

This application claims priority to and the benefit of Korean Patent Application No. 10-2005-0038799 filed in the Korean Industrial Property Office on May 10, 2005, the entire contents of which are incorporated hereinto by reference.

BACKGROUND OF THE INVENTION (a) Field of the Invention

The present invention relates to a method and an apparatus for continuously separating aromatic dialdehyde from a reaction mixture obtained by gas-phase oxidation of dimethylbenzene in the presence of a catalyst.

(b) Description of the Related Art

Among aromatic compounds, aromatic aldehydes find many uses because they have highly reactive aldehyde groups.

Aromatic dialdehydes, particularly terephthalaldehyde, are bifunctional compounds that have gained attention as an ingredient for a variety of new materials. For example, they are used in liquid crystals, conductive polymers, high-temperature engineering polymers, medicines, agrochemicals, dyes, fluorescent brighteners and specialty polymers.

U.S. Pat. No. 4,465,865 discloses a method of preparing aromatic dialdehydes in an aqueous solution that includes photo-chlorination and hydrolysis. p-Xylene or m-xylene is chlorinated at 80-90° C. by irradiation with UV to obtain several chlorinated compounds. The chlorinated compounds are mixed with an aqueous solution of hexamethylenetetramine and stirred at 100-115° C. to obtain aromatic dialdehydes. The reaction mixture including the aromatic dialdehydes is cooled and filtered to obtain aromatic dialdehydes in solid phase.

When aromatic dialdehydes are prepared in liquid phase and recrystallized by cooling, unwanted byproducts tend to be precipitated along with the aromatic dialdehydes. In such a case, the aromatic dialdehydes may be selectively separated by extraction with a specific solvent, as presented in the examples of U.S. Pat. No. 2,888,488.

U.S. Pat. No. 6,458,737 discloses a method of obtaining terephthalaldehyde along with the p-tolualdehyde byproduct by collecting a reaction gas mixture being discharged from a reactor with cooled methanol. This method is disadvantageous in that a process of separating the terephthalaldehyde from the p-tolualdehyde is required additionally.

U.S. Pat. No. 3,845,137 discloses a method of preparing multifunctional aromatic aldehydes by gas-phase oxidation. This method needs a long reaction time and is inadequate for continuous preparation of aromatic aldehydes because the aromatic aldehydes are not selectively separated from the reaction product.

SUMMARY OF THE INVENTION

In view of the above state of the art, the present invention provides a method for separating an aromatic dialdehyde from a gas-phase mixture that includes introducing a gas-phase mixture including an aromatic dialdehyde that is obtained by gas-phase oxidation of dimethylbenzene into a condenser, selectively congealing the aromatic dialdehyde by cooling the mixture and collecting the congealed aromatic dialdehyde at the bottom of the condenser by gravity in the form of powder or flakes, while discharging the remaining gas-phase mixture out of the condenser.

The present invention provides a method for continuously separating an aromatic dialdehyde, which includes the steps of:

(a) introducing a gas-phase reaction mixture including an aromatic dialdehyde that is obtained by gas-phase oxidation of dimethylbenzene into a condenser and selectively congealing the aromatic dialdehyde by cooling the mixture to 5-70° C.; and (b) separating the congealed aromatic dialdehyde from the gas-phase reaction mixture.

The present invention also provides an apparatus for continuously separating an aromatic dialdehyde from a reaction mixture obtained by gas-phase oxidation of dimethylbenzene that includes a condenser for cooling the reaction mixture so that at least part of the aromatic dialdehyde included in the reaction mixture is congealed and a cyclone for separating and discharging the congealed aromatic dialdehyde included in the cooled reaction mixture.

The present invention further provides an apparatus for continuously separating an aromatic dialdehyde from a reaction mixture obtained by gas-phase oxidation of dimethylbenzene that includes a condenser for cooling the reaction mixture so that at least part of the aromatic dialdehyde included in the reaction mixture is congealed and selectively discharging the congealed aromatic dialdehyde settled by gravity.

DETAILED DESCRIPTION OF THE PREFERRED EMBODIMENTS

Figure 1:
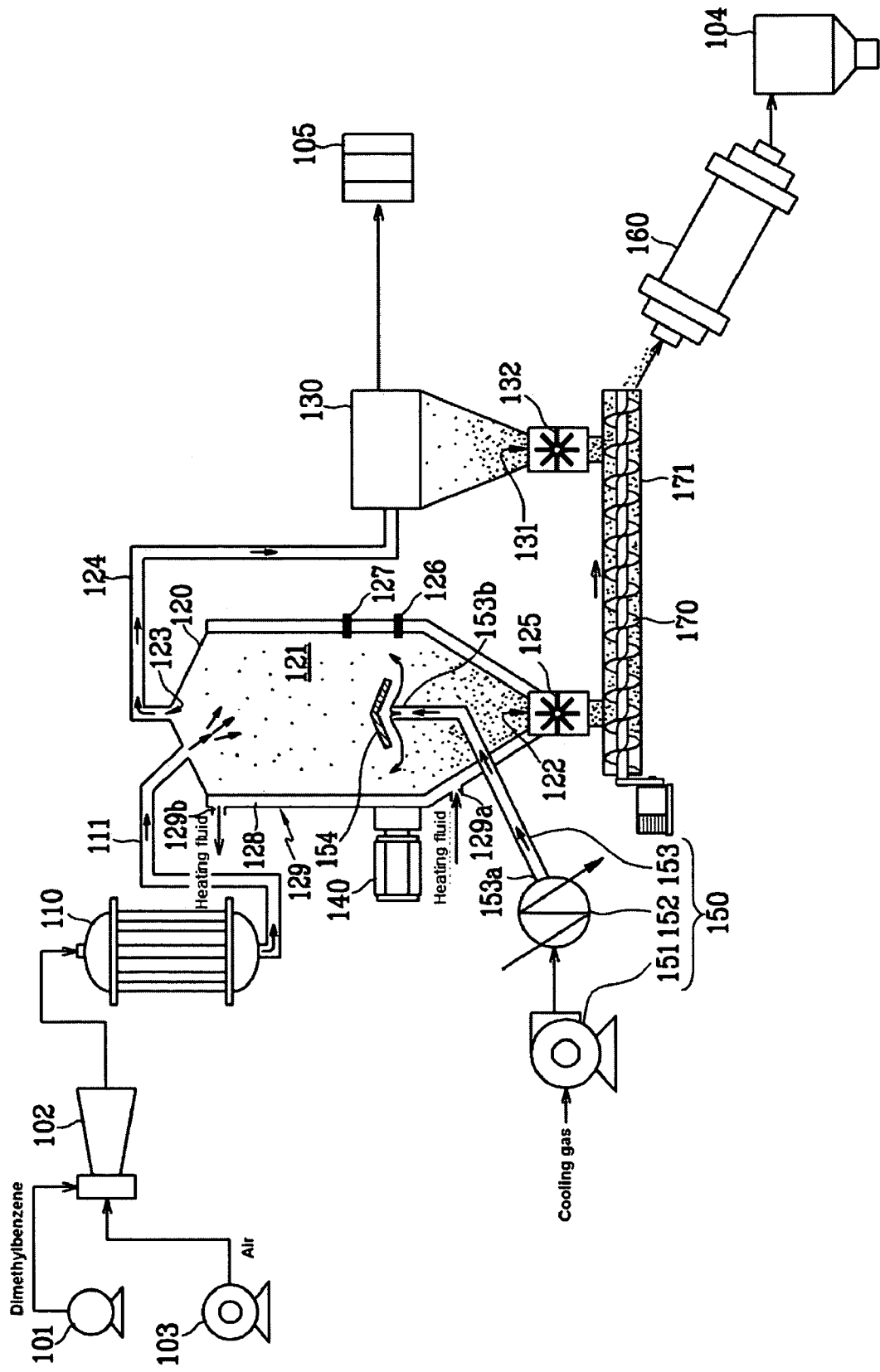
FIG. 1 is a schematic diagram illustrating the process of preparing an aromatic dialdehyde using an apparatus for separating the aromatic dialdehyde in accordance with an embodiment of the present invention.

In the method for separating an aromatic dialdehyde of the present invention, the gas-phase reaction mixture of step (a) may be obtained by reacting molecular oxygen with dimethylbenzene in gaseous phase at 400-600° C. in the presence of an oxidation catalyst.

The catalyst may be an oxide catalyst, such as a tungsten oxide- or molybdenum oxide-based catalyst. The gas-phase reaction mixture is introduced into the condenser at 200-350° C.

In addition to the methylbenzene and molecular oxygen, a diluent gas may be used in the gas-phase oxidation, if required. Air or pure oxygen may be used as a source of the molecular oxygen. In general, the molecular oxygen is used in 5-50 moles per 1 mole of methylbenzene. For the diluent gas, such inert gases as nitrogen, helium, argon and $CO_2$, water vapor, etc., may be used.

The reaction condition of the gas-phase oxidation is not particularly restricted. For example, the source gas may be contacted with the oxidation catalyst at a space velocity of 1000-100000 $hr^{-1}$ at 350-650° C., more preferably at a space velocity of 1000-20000 $hr^{-1}$ at 400-600° C. The reaction is usually performed at normal pressure, but it may also be performed at a slightly elevated or reduced pressure.

The type of the reactor is not particularly restricted, either. Any of a fixed-bed type, a moving-bed type, or a fluid bed type reactor may be used. Also, either a one pass reactor or a recycle reactor may be used.

In the gas-phase oxidation of dimethylbenzene, for example, in preparation of terephthalaldehyde from gas-phase oxidation of p-xylene, such byproducts as benzaldehyde, p-tolualdehyde, p-hydroxybenzaldehyde, hydroquinone, 4-carboxybenzaldehyde, carbon monoxide, and carbon dioxide are formed. The present invention is advantageous in that high-purity terephthalaldehyde can be obtained in solid phase without an additional purification process.

Also, in step (a), the gas-phase reaction mixture is cooled to 5-70° C., preferably to 20-60° C. If the cooling temperature is below 5° C., excessive energy or cooling gas has to be consumed. In contrast, if it exceeds 70° C., the aromatic dialdehyde may not be sufficiently congealed.

The cooling in step (a) may be performed indirectly by cooling the condenser or directly by cooling the gas-phase reaction mixture by injecting a cooling gas into the condenser. The indirect cooling may be performed by circulating a coolant in a jacket installed outside the condenser. The direct cooling may be performed by injecting a gas, for example, air, nitrogen, carbon dioxide, argon, helium, etc., cooled by a heat exchanger into the condenser and contacting it with the reaction mixture in gas phase. However, these cooling methods are not restrictive examples.

In an embodiment of the present invention, the separation step (b) may be performed by separating the congealed aromatic dialdehyde from the gas-phase mixture.

In another embodiment of the present invention, the separation step (b) may be performed by collecting the aromatic dialdehyde congealed in step (a) at the bottom of the condenser by gravity and discharging the remaining gas-phase mixture out of the condenser. Alternatively, the congealed aromatic dialdehyde may be discharged out of the condenser along with the remaining gas-phase reaction mixture and separated by a cyclone directly coupled at the bottom of the condenser.

The separation step (b) may be performed by discharging the congealed aromatic dialdehyde settled at the bottom of the condenser by gravity out of the condenser, discharging the remaining gas-phase mixture at the top of the condenser and further separating the congealed aromatic dialdehyde using a cyclone.

The dimethylbenzene used in the present invention is a compound having two methyl groups directly bonded to the benzene ring, for example, p-xylene, m-xylene. Also, the aromatic dialdehyde prepared from the dimethylbenzene may be terephthalaldehyde prepared from p-xylene, isophthalaldehyde prepared from m-xylene, etc.

The apparatus for separating an aromatic dialdehyde according to an embodiment of the present invention includes a condenser for cooling a reaction mixture obtained by gas-phase oxidation of dimethylbenzene so that at least part of the aromatic dialdehyde included in the reaction mixture can be congealed.

The apparatus for separating another aromatic dialdehyde according to an embodiment of the present invention may further include a cyclone for separating and discharging the congealed aromatic dialdehyde included in the reaction mixture cooled by the condenser.

The condenser may have a first discharge path for discharging the congealed aromatic dialdehyde settled at the bottom of the condenser by gravity and a second discharge path for discharging the remaining reaction gas mixture. The cyclone may separate and discharge the congealed aromatic dialdehyde included in the reaction mixture discharged through the second discharge path.

The condenser may have a first on/off valve for opening or closing the first discharge path.

The cyclone may have a third discharge path for discharging the congealed aromatic dialdehyde separated by the cyclone and a second on/off valve for opening or closing the third discharge path.

The condenser may further include a level detector for detecting the height level of the congealed aromatic dialdehyde settled at the bottom of the condenser.

In the apparatus for separating an aromatic dialdehyde according to another embodiment of the present invention, the condenser may have a first discharge path for discharging the cooled reaction mixture and the cyclone may separate and discharge the congealed aromatic dialdehyde included in the reaction mixture discharged through the first discharge path by centrifuge.

The cyclone may have a second discharge path for discharging the congealed aromatic dialdehyde separated by the cyclone and an on/off valve for opening or closing the second discharge path.

The apparatus for separating an aromatic dialdehyde of the present invention may further include a cooling gas feeder for feeding a cooling gas to cool the reaction mixture into the condenser.

Further, the cooling gas feeder may include a blower for blowing the cooling gas, a heat exchanger for cooling the cooling gas supplied from the blower by heat exchange and a cooling gas supply pipe for supplying the cooling gas supplied from the heat exchanger into the condenser. One end of the cooling gas supply pipe is connected to the heat exchanger and the other end is connected to the condenser.

A dispersion plate may be installed inside the condenser to disperse the cooling gas supplied from the cooling gas supply pipe. The dispersion panel may be positioned at the upper end of the cooling gas supply pipe.

The apparatus for separating an aromatic dialdehyde according to the present invention may further include a jacket for transferring heat to the condenser or for providing a path for a heating fluid that absorbs heat from the condenser.

Hereinafter, the present invention is described in further detail referring to the attached drawings.

Figure 2:
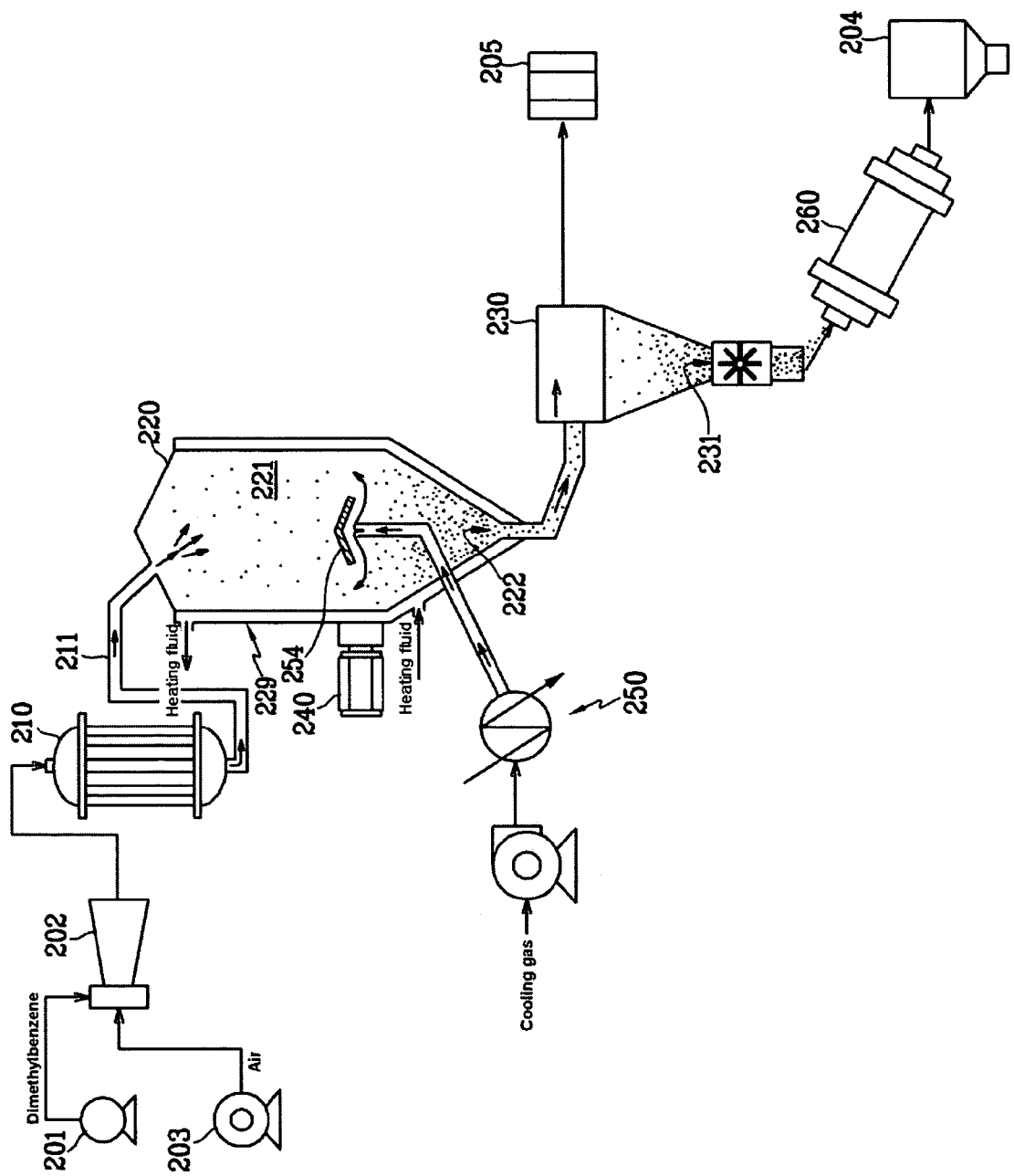
FIG. 2 is a schematic diagram illustrating the process of preparing an aromatic dialdehyde using the apparatus for separating the aromatic dialdehyde in accordance with another embodiment of the present invention.

Referring to FIG. 1 and FIG. 2, the apparatus for separating an aromatic dialdehyde in accordance with the present invention includes a condenser (120, 220). The condenser (120, 220) congeals at least part of the gaseous aromatic dialdehyde included in the reaction mixture obtained by gas-phase oxidation of dimethylbenzene ($C_6H_4(CH_3)$). The condenser (120, 220) may be, for example, a cooling tower.

In another embodiment of the present invention, the apparatus for separating an aromatic dialdehyde may further include a cyclone (130, 230) for further separating the congealed aromatic dialdehyde included in the cooled reaction mixture discharged from the condenser (120, 220).

For example, the reaction mixture obtained by gas-phase oxidation of dimethylbenzene may be supplied to the condenser (120, 220) by an oxidation reactor (110, 210).

Aromatic dialdehyde is a compound in which two hydrogen atoms of benzene ($C_6H_6$) are substituted with aldehyde (—CHO) groups. For example, terephthalaldehyde, and isophthalaldehyde are aromatic dialdehydes.

Referring to FIG. 1, dimethylbenzene is supplied to a mixer (102), being pumped by a pump (101). Air compressed by a compressor (103) may also be supplied to the mixer (102).

The mixer (102) mixes the dimethylbenzene with the air and the dimethylbenzene-air mixture is supplied to an oxidation reactor (110).

The oxidation reactor induces catalytic gas-phase oxidation of the dimethylbenzene-air mixture supplied by the mixer (102). The reaction mixture obtained by the gas-phase oxidation of dimethylbenzene includes an aromatic dialdehyde. Temperature inside the oxidation reactor (110) may be kept at about 600° C. The aromatic dialdehyde included in the reaction mixture is in gaseous state. For example, the gas-phase reaction mixture including aromatic dialdehyde may be obtained by reacting molecular oxygen and dimethylbenzene in gaseous phase at 400-600° C. in the presence of an oxidation catalyst. The oxidation reactor (110) used in the gas-phase oxidation of dimethylbenzene may be a fixed-bed catalyst reactor including multitubes that control the reaction temperature with molten salt.

The reaction mixture including the gaseous aromatic dialdehyde is discharged from the oxidation reactor (110) and is supplied to a congealing chamber (121) inside the condenser (120) via a connection pipe (111). Temperature inside the connection pipe (111) may be maintained above a predetermined temperature so that the gaseous aromatic dialdehyde included in the reaction mixture is not congealed while passing through the connection pipe (111). For example, the connection pipe (111) may be thermally insulated or be equipped with a heater in order to maintain the temperature of the reaction mixture passing through the connection pipe (111) above a predetermined value. The predetermined temperature may range from 200 to 350° C., more specifically, from 250 to 300° C. Also, temperature at the top of the condenser may be maintained above a predetermined temperature, for example, at about 150-250° C., so that the reaction mixture is not congealed there.

The condenser (120) cools the reaction mixture supplied through the connection pipe (111). For example, the condenser (120) may cool the reaction mixture to about 5-70° C. As the reaction mixture is cooled in the congealing chamber (121), most of the gaseous aromatic dialdehyde included in the reaction mixture is congealed (or desublimed) to solid aromatic dialdehyde.

The congealed aromatic dialdehyde settles at the bottom of the congealing chamber (121) by gravity.

The condenser (120) may have two discharge paths (122, 123); a first discharge path (122) for discharging the congealed aromatic dialdehyde settled at the bottom of the condenser by gravity and a second discharge path (123) for discharging the remaining reaction mixture. For example, as illustrated in FIG. 1, the first discharge path (122) may be positioned at the bottom of the condenser (120) and the second discharge path (123) may be positioned at the top of the condenser (120).

The remaining reaction mixture discharged by the second discharge path (123) is supplied to a cyclone (130) via a connection pipe (124). The cyclone (130) separates and discharges the congealed aromatic dialdehyde included in the remaining reaction mixture by centrifuge.

The congealed aromatic dialdehyde separated by the cyclone (130) falls down and is discharged via a discharge path (131).

The condenser (120) has a first on/off valve (125) that opens or closes the first discharge path (122). For example, the first on/off valve (125) may be a rotary valve. When the first on/off valve (125) opens, the congealed aromatic dialdehyde settled at the bottom of the congealing chamber (121) is discharged via the first discharge path (122), and when the first on/off valve (125) closes, discharge of the congealed aromatic dialdehyde is stopped. The efficiency of the condenser (120) can be improved by opening and closing the first on/off valve (125) at the right time. If the first on/off valve (125) is a rotary valve, discharge of the accumulated congealed aromatic dialdehyde can be more efficient.

Further, the cyclone (130) has a second on/off valve (132) that opens or closes the third discharge path (131). For example, the second on/off valve (132) may be a rotary valve. When the second on/off valve (132) opens, the congealed aromatic dialdehyde settled at the bottom of the cyclone (130) is discharged via the discharge path (131), and when the second on/off valve (132) closes, discharge of the congealed aromatic dialdehyde is stopped. If the second on/off valve (132) is a rotary valve, discharge of the accumulated congealed aromatic dialdehyde can be more efficient.

As illustrated in FIG. 1, the apparatus for separating an aromatic dialdehyde of the present invention may further include a vibrator (140) that is attached to the condenser (120) and generates mechanical vibration. The mechanical vibration transferred from the vibrator (140) to the condenser (120) helps the congealed aromatic dialdehyde sticking to the inner wall of the condenser (120) to be detached. Consequently, the efficiency of the apparatus for separating an aromatic dialdehyde is improved.

The apparatus for separating an aromatic dialdehyde of the present invention may further include a cooling gas feeder (150) that supplies gas for cooling the reaction mixture supplied to the condenser (120) into the congealing chamber (121). In addition to the cooling by the condenser (120), the cooling gas feeder (150) enables more effective cooling of the reaction mixture. The cooling gas may be, for example, air or nitrogen.

The cooling gas feeder (150) includes a blower (151), a heat exchanger (152), and a cooling gas supply pipe (153), as illustrated in FIG. 1. The blower (151) compresses and blows the cooling gas and the heat exchanger (152) cools the cooling gas supplied from the blower (151) by heat exchange. The cooling gas supply pipe (153) supplies the cooling gas discharged from the heat exchanger (152) to the congealing chamber (121) inside the condenser (120). For example, one end (153a) of the cooling gas supply pipe (153) may be connected to the outlet of the heat exchanger (152) and the other end (153b) may be connected to the congealing chamber (121).

Also, a dispersion panel (154) for dispersing the cooling gas supplied via the cooling gas supply pipe (153) is installed in the congealing chamber (121) inside the condenser (120). The dispersion panel (154) is installed at the front of the outlet (153b) of the cooling gas supply pipe (153) so that the cooling gas discharged from the outlet (153b) of the cooling gas supply pipe (153) is dispersed uniformly after colliding against the dispersion panel (154). As a result, the reaction mixture can be cooled more uniformly by the so-dispersed cooling gas. Although not illustrated in the figure, it is appreciated that the dispersion panel (154) can be installed in the congealing chamber (121) by any method. For example, the dispersion panel (154) may be installed on the frame connected with the inner wall of the condenser (120) or may be installed connected with the cooling gas supply pipe (153).

Further, as illustrated in FIG. 1, the dispersion panel (154) is preferably positioned above the outlet (153b) of the cooling gas supply pipe (153). This construction can minimize the flow of the free-falling congealed aromatic dialdehyde, which has been congealed in the congealing chamber (121), into the cooling gas supply pipe (153).

That is, in the present invention, the gas-phase reaction mixture is cooled indirectly by cooling the condenser or directly by injecting the cooling gas into the cooling gas feeder.

At least one level detector (126,127) may be installed in the condenser (120), which detects the height level of the congealed aromatic dialdehyde settled at the bottom of the congealing chamber (121). The action of the first on/off valve (125) may be controlled depending on the height level of the congealed aromatic dialdehyde detected by the level detector (126,127). Preferably, an external control unit (not illustrated in the figure) controls the action of the first on/off valve (125) depending on the signal transferred from the level detector (126,127). For example, the control unit may control the action of the first on/off valve (125) so that the first on/off valve (125) operates faster when an upper level detector (127) detects the congealed aromatic dialdehyde than when a lower level detector (126) detects the congealed aromatic dialdehyde. Also, the lower level detector (126) may be installed at a position lower than the dispersion panel (154) in order to prevent the accumulated congealed aromatic dialdehyde from flowing into the cooling gas supply pipe (153).

Further, the condenser (120) may be equipped with a jacket (129) which provides a heating fluid path (128). Heating fluid is injected into the inlet (129a) and discharged at the outlet (129b). As the heating fluid flows along the heating fluid path (128), it absorbs or provides heat from or to the housing of the condenser (120). Through the control of the temperature of the housing with the heating fluid, detachment of the congealed aromatic dialdehyde sticking to the inner wall of the condenser (120) may be facilitated.

The apparatus for separating an aromatic dialdehyde according to the present invention may further include a dryer (160) for drying the congealed dialdehyde discharged through the discharge path (122) of the condenser (120) and the discharge path (131) of the cyclone (130).

Also, the apparatus for separating an aromatic dialdehyde according to the present invention may further include a conveyor (170) for conveying the congealed aromatic dialdehyde discharged from the condenser (120) and the cyclone (130) to the dryer (160). As illustrated in FIG. 1, the conveyor (170) is positioned below the condenser (120) and the cyclone (130) and conveys the congealed aromatic dialdehyde discharged from the condenser (120) and the cyclone (130) to the dryer (160). For example, the conveyor (170) may be a screw conveyor. As illustrated in FIG. 1, the conveyor (170) may be installed inside a tube (171) so that the congealed aromatic dialdehyde is conveyed within the tube (171).

The congealed aromatic dialdehyde dried by the dryer (160) may be transferred to a container (104) and stored therein.

Also, the remaining gas discharged from the cyclone (130) may be transferred to an incinerator (105) and burned therein.

Now, another embodiment of the present invention is described referring to FIG. 2.

Referring to FIG. 2, dimethylbenzene may be pumped into a mixer (202) by a pump (201) and compressed air may be supplied to the mixer (202) by a compressor (203). The mixer (202) mixes the dimethylbenzene with the air and the resultant dimethylbenzene-air mixture is supplied to an oxidation reactor (210). The reaction mixture including gaseous aromatic dialdehyde is discharged from the oxidation reactor (210) and is supplied to a congealing chamber (221) inside a condenser (220) via a connection pipe (211). Description of the construction and operation of the pump (201), the mixer (202), the compressor (203), the oxidation reactor (210), and the connection pipe (211) is omitted since they are the same as in FIG. 1.

The condenser (220) cools the reaction mixture supplied via the connection pipe (211). For example, the condenser (220) may cool the reaction mixture to about 5-70° C. As the reaction mixture is cooled in the congealing chamber (221) inside the condenser (220), most of the gaseous aromatic dialdehyde included in the reaction mixture is congealed or desublimed to solid aromatic dialdehyde.

The condenser (220) may have a discharge path (222) through which the cooled reaction mixture is discharged. For example, the discharge path (222) may be formed at the bottom of the condenser (220).

The cyclone (230) separates the congealed aromatic dialdehyde included in the reaction mixture, which has been discharged through the discharge path (222), by centrifuge and discharges it.

The congealed aromatic dialdehyde separated by the cyclone (230) falls down and is discharged via a discharge path (231).

The cyclone (230) has an on/off valve (232) that opens or closes the discharge path (231). For example, the on/off valve (232) may be a rotary valve.

The congealed aromatic dialdehyde discharged via the discharge path (231) of the cyclone (230) is supplied to a dryer (260) and is dried therein.

As in FIG. 1, the congealed aromatic dialdehyde dried by the dryer (260) may be supplied to a container (204) and stored therein. Also, the remaining gas discharged from the cyclone (230) may be supplied to an incinerator (205) and burned therein.

Also, as in FIG. 1, the apparatus for separating an aromatic dialdehyde according to this embodiment may further include at least one of a vibrator (240), a cooling gas feeder (250), a dispersion panel (254), and a jacket (229). Description of the construction and operation of them is omitted since they are the same as in FIG. 1.

EXAMPLES

Example 1

Terephthalaldehyde was prepared by gas-phase oxidation of p-xylene using a bench-scale apparatus. The gaseous mixture including terephthalaldehyde was condensed and separated to obtain a solid product.

To be more specific, p-xylene was fed to the reaction apparatus in gas phase along with air. A fixed-bed catalytic reactor was used and a $WO_3/Al_2O_3$ catalyst prepared by immersing 5-mm spherical α-alumina in aqueous ammonium metatungstate solution was used as a catalyst.

Reaction temperature was controlled with molten salt. Flow rate of p-xylene was maintained at 2.7 cc/hr using a syringe pump. p-Xylene was mixed with air after being passed through an evaporator heated to 150° C.

The mixture of p-xylene and air was injected into the reactor (1200 cc/min) after being preheated to 200° C.

Reaction temperature was maintained at 580° C. The reaction mixture obtained by the gas-phase oxidation was introduced into a condenser at room temperature after passing through a transfer line heated at 350° C.

In the condenser, condensable (or desublimable) compounds including terephthalaldehyde were condensed and separated from the reaction mixture as a solid (including trace liquid) and the remaining mixture was transferred to a collecting apparatus.

In the collecting apparatus, the reaction mixture was dissolved with methanol to collect the remaining product and the remaining gas was vented out.

The reaction product was analyzed by "on-line GC". The solid compound condensed by the condenser and the solid compound obtained by the dissolution with methanol were weighed and analyzed by "GC-mass spectroscopy".

Table 1 below shows the analysis result of the reaction product obtained by gas-phase oxidation of p-xylene.

Table 2 below shows the weight of the solid compound collected by the condenser and the collecting apparatus, and, Table 3 shows the composition of the solid compound collected by the condenser and the collecting apparatus.

TABLE 1

Composition of gas-phase oxidation product of p-xylene before being introduced to the condenser (mol %)

| p-Xylene Conv. | Selectivity | | | | | | | TPAL yield |
|---|---|---|---|---|---|---|---|---|
| | TPAL | PTAL | CO | $CO_2$ | BAL | 4-CBA | Unknown | |
| 82.9 | 66.9 | 3.1 | 7.9 | 17.1 | 1.8 | 2.7 | 0.5 | 55.5 |

TPAL: terephthalaldehyde
PTAL: p-tolualdehyde
BAL: benzaldehyde
4-CBA: 4-carboxybenzaldehyde

TABLE 2

| Weight of solid product | |
|---|---|
| Weight of solid product | 72.9 g (62 g from the condenser, 10.9 g from the collecting apparatus) |
| Weight of collected TPAL | 70.8 g |
| Weight of produced TPAL | 82.0 g |
| TPAL recovery rate | 86.3% |

In Table 2, the following equations were used for the calculations.

Weight of solid product=Weight of solid collected by the condenser+weight of solid collected by the collecting apparatus Weight of collected $TPAL$=Weight of solid product× $TPAL$ content in the solid (%)

Weight of produced $TPAL$=$TPAL$ yield analyzed by GC×amount of supplied p-xylene (g)×$M_t/M_p$ ($M_t$: molecular weight of $TPAL$, $M_p$: molecular weight of p-xylene)

$TPAL$ recovery rate=Weight of collected $TPAL$/weight of produced $TPAL$×100

TABLE 3

| Composition of solid product | |
|---|---|
| Solid components | Content (wt %) |
| TPAL | 97.1 |
| PTAL | 1.22 |
| 4-CBA | 1.00 |
| Others | 0.68 |

As apparent from the above description, the present invention enables selective separation of aromatic dialdehyde from a reaction mixture obtained by gas-phase oxidation of dimethylbenzene.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for continuously separating an aromatic dialdehyde comprising the steps of:
   (a) introducing a gas-phase reaction mixture obtained by gas-phase oxidation of dimethylbenzene into a condenser and selectively congealing an aromatic dialdehyde from the gas-phase reaction mixture by cooling it to 5-70° C.; and
   (b) separating the congealed aromatic dialdehyde from the remaining gas-phase reaction mixture by cyclone.

2. The method for continuously separating an aromatic dialdehyde as set forth in claim 1, wherein the gas-phase reaction mixture of step (a) is prepared by reacting molecular oxygen with dimethylbenzene in gaseous phase at 350-650° C. in the presence of an oxidation catalyst.

3. The method for continuously separating an aromatic dialdehyde as set forth in claim 1, wherein the temperature of the gas-phase reaction mixture introduced to the condenser ranges from 200 to 350° C.

4. The method for continuously separating an aromatic dialdehyde as set forth in claim 1, wherein in step (a), the cooling step of the gas-phase reaction mixture is performed indirectly by cooling the condenser or directly by injecting a cooling gas into the condenser.

5. The method for continuously separating an aromatic dialdehyde as set forth in claim 1, wherein the separation of step (b) is performed by collecting the congealed congealed aromatic dialdehyde at the bottom of the condenser as it falls down by gravity and discharging the remaining gas-phase reaction mixture from the condenser.

6. The method for continuously separating an aromatic dialdehyde as set forth in claim 1, wherein the separation of step (b) is performed by discharging the congealed aromatic dialdehyde along with the remaining gas-phase reaction mixture to the condenser and separating the congealed aromatic dialdehyde at a cyclone directly coupled to the condenser at the bottom of the condenser.

7. The method for continuously separating an aromatic dialdehyde as set forth in claim 1, wherein the separation of step (b) is performed by separating the congealed aromatic dialdehyde, settled at the bottom of the condenser by gravity, by discharging it out of the condenser and further separating the congealed aromatic dialdehyde using a cyclone as the remaining gas-phase reaction mixture is discharged from the upper part of the condenser.

* * * * *